United States Patent [19]

Henke et al.

[11] Patent Number: 5,422,342

[45] Date of Patent: Jun. 6, 1995

[54] 2,3-DISUBSTITUTED ISOXAZOLIDINES, A AGENTS CONTAINING THEM AND THEIR USE

[75] Inventors: Stephan Henke, Bad Soden am Taunus; Dietrich Brocks, Wiesbaden; Volkmar Günzler, Marburg-Cappel, all of Germany

[73] Assignee: Hoechst Aktiengesellschaft, Frankfurt am Main, Germany

[21] Appl. No.: 47,074

[22] Filed: Apr. 16, 1993

Related U.S. Application Data

[63] Continuation of Ser. No. 133,273, Dec. 15, 1987, abandoned.

[30] Foreign Application Priority Data

Dec. 17, 1986 [DE] Germany .................. 36 43 012.9

[51] Int. Cl.⁶ .................. A61K 38/05; A61K 38/06; C07D 261/02
[52] U.S. Cl. .................. 514/18; 514/19; 514/378; 530/331; 548/240
[58] Field of Search .......... 548/240, 243, 246; 514/378, 380, 18, 19; 530/331

[56] References Cited

U.S. PATENT DOCUMENTS

| | | | |
|---|---|---|---|
| 3,944,562 | 3/1976 | Martin et al. | 548/240 X |
| 4,269,772 | 5/1981 | Melillo et al. | 548/240 X |
| 4,457,936 | 7/1984 | Draeger et al. | 548/200 X |
| 4,562,187 | 12/1985 | Tegeler et al. | 514/378 X |

FOREIGN PATENT DOCUMENTS 3643957  6/1988  Germany .................. 548/240

OTHER PUBLICATIONS

V. Gunzler et al, The Journal of Biological Chemistry, vol. 263, No. 36, pp. 19498–19504, 1988.
A. Vessella et al., Chemical Abstracts, vol. 95, No. 7, p. 706, 95:62045p (1981).
A. Vessella et al., Chemical Abstracts, vol. 99, No. 19, p. 654 99:158804u (1983).

*Primary Examiner*—Joseph Paul Brust
*Attorney, Agent, or Firm*—Finnegan, Henderson, Farabow, Garrett & Dunner

[57] ABSTRACT

The invention relates to compounds of the formula

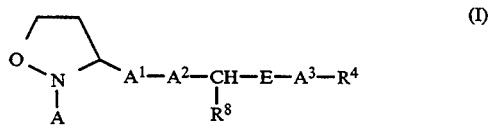

(I)

in which A denotes an optionally substituted radical from the series comprising alkyl, acyl, cycloalkyl, aryl and heteroaryl; $A^1$ represents CO, CS, C=NH, CN-alkyl, CN-O-alkyl, SO, optionally substituted $CH_2$ or a bond; $A^2$ represents NH, $NCH_3$, O, $CH_2$ or a bond; E represents CHOH, CO, SO or optionally N-substituted C=NH; $A^3$ represents O, NH, $NCH_3$ or a bond; $R^4$ denotes an optionally substituted radical from the series comprising alkyl, cycloalkyl, aryl and heteroaryl; and $R^8$ denotes hydrogen or optionally substituted alkyl, to a process for their preparation, and to their use as inhibitors of prolyl hydroxylase.

19 Claims, No Drawings

2,3-DISUBSTITUTED ISOXAZOLIDINES, AGENTS CONTAINING THEM AND THEIR USE

This application is a continuation of application Ser. No. 07/133,273, filed Dec. 15, 1987, now abandoned.

U.S. Pat. No. 4,457,936 discloses hydroxyphenyl-thiazole-, -thiazoline- and -thiazolidine-carboxylic acids and their use as inhibitors of, inter alia, prolyl hydroxylase.

It has been found that isoxazolidine derivatives which are substituted in a particular manner are highly effective suicide inhibitors of prolyl hydroxylase. Hence the invention relates to compounds of the formula I

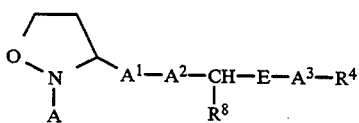

in which

A denotes a1) $(C_1-C_8)$-alkyl, $(C_1-C_8)$-alkanoyl, $(C_1-C_8)$-alkoxycarbonyl or $(C_1-C_8)$-alkyl sulfonyl, in each of which 1, 2 or 3 hydrogen atoms are optionally replaced by 1, 2 or 3 identical or different radicals from the series comprising carboxyl, amino, $(C_1-C_4)$-alkylamino, hydroxyl, $(C_1-C_4)$-alkoxy, halogen, di-$(C_1-C_4)$-alkylamino, carbamoyl, sulfamoyl, $(C_1-C_4)$-alkoxycarbonyl, $(C_6-C_{12})$-aryl and ($C_6-C_{12}$)-aryl-$(C_1-C_5)$-alkyl, or in each of which 1 hydrogen atom is optionally replaced by a radical from the series comprising $(C_3-C_8)$-cycloalkyl, $(C_1-C_4)$ alkylsulfonyl, $(C_1-C_4)$-alkylsulfinyl, $(C_6-C_{12})$-aryl-$(C_1-C_4)$-alkylsulfonyl, $(C_6-C_{12})$-aryl-$(C_1-C_4)$-alkylsulfinyl, $(C_6-C_{12})$-aryloxy, $(C_3-C_9)$-heteroaryl and $(C_3-C_9)$-heteroaryloxy, and 1 or 2 hydrogen atoms are replaced by 1 or 2 identical or different radicals from the series comprising carboxyl, amino, $(C_1-C_4)$-alkylamino, hydroxyl, $(C_1-C_4)$-alkoxy, halogen, di-$(C_1-C_4)$-alkylamino, carbamoyl, sulfamoyl, $(C_1-C_4)$-alkoxycarbonyl, $(C_6-C_{12})$-aryl and $(C_6-C_{12})$-aryl-$(C_1-C_5)$-alkyl, denotes a2) $(C_3-C_8)$-cycloalkyl, $(C_6-C_{12})$-aryl, $(C_6-C_{12})$-arylsulfonyl or $(C_3-C_9)$-heteroaryl, each of $(C_6-C_{12})$-aryl or $(C_3-C_9)$-heteroaryl in the radicals defined under a1) and a2) being optionally substituted by 1, 2 or 3 identical or different radicals from the series comprising carboxyl, amino, nitro, $(C_1-C_4)$-alkylamino, hydroxyl, $(C_1-C_4)$-alkoxy, halogen, cyano, di-$(C_1-C_4)$-alkylamino, carbamoyl, sulfamoyl and $(C_1-C_4)$-alkoxycarbonyl, or denotes a3) a radical of the formula IIa or IIb

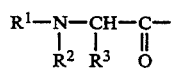

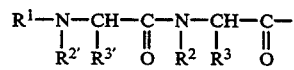

$R^1 b_1$) denotes hydrogen or
b2) is defined as A under a1) or a2),
c1) $R^2$ and $R^{2'}$ are identical or different and denote hydrogen or methyl, $R^3$ and $R^{3'}$ are identical or different and denote hydrogen or $(C_1-C_6)$-alkyl, preferably $(C_1-C_4)$-alkyl, which is optionally monosubstituted by amino, benzyloxycarbonylamino, hydroxyl, carboxyl, carbamoyl, guanidino, ureido, mercapto, methylmercapto, phenyl, 4-chlorophenyl, 4-fluorophenyl, 4-nitrophenyl, 4-methoxyphenyl, 4-hydroxyphenyl, phthalimido, 4-imidazolyl, 3-indolyl, 2-thienyl, 3-thienyl, 2-pyridyl, 3-pyridyl or cyclohexyl, c2) $R^2$ and $R^3$ and/or $R^{2'}$ and $R^{3'}$ in each case together represent a [—$CH_2$—$CH_2$—$CH_2$—]chain in which a $CH_2$ group can be replaced by 0, or c3) $R^2$ and $R^3$ and/or $R^{2'}$ and $R^{3'}$ in each case together represent

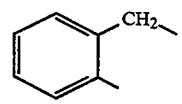

$A^1$ denotes carbonyl, thiocarbonyl, carbimidoyl, N-$(C_1-C_3)$-alkyl carbimidoyl, N-$(C_1-C_3)$-alkoxycarbimidoyl, sulfinyl, $CR^5R^6$ or a direct bond, d1) $R^5$ and $R^6$ are identical or different and denote hydrogen, $(C_1-C_8)$-alkyl or $(C_3-C_8)$-cycloalkyl, or d2) $R^5$ and $R^6$ together represent —$[CH_2]_m$— with m=4 or 5, in which 1 or 2 $CH_2$ groups are optionally replaced by 0, S and/or $NR^7$, $A^2$ denotes imino, N-methylimino, oxy, methylene or a direct bond, E denotes carbonyl, $C=NR^7$, $C=N—OR^7$ or sulfinyl, or, if $A^3$ represents a bond, can also denote hydroxymethylene, $R^7$ is defined as $R^5$ under d1), $A^3$ denotes oxy, imino, N-methylimino or a direct bond, $R^4$ denotes $(C_1-C_6)$-alkyl, $(C_3-C_6)$-cycloalkyl, $(C_6-C_{12})$-aryl, $(C_6-C_{12})$-aryl-$(C_1-C_5)$-alkyl, $(C_6-C_{12})$-aryloxy-$(C_1-C_5)$-alkyl, $(C_3-C_9)$-heteroaryl or $(C_3-C_9)$-heteroaryl-$(C_1-C_5)$-alkyl, in which each alkyl is optionally substituted by 1 or 2 identical or different radicals from the series comprising carboxyl, amino, $(C_1-C_4)$-alkylamino, hydroxyl, $(C_1-C_4)$-alkoxy, halogen, di-$(C_1-C_4)$-alkylamino, carbamoyl, sulfamoyl, $(C_1-C_4)$-alkoxycarbonyl, $(C_6-C_{12})$-aryl and $(C_6-C_{12})$-aryl-$(C_1-C_5)$-alkyl, and in which each $(C_6-C_{12})$-aryl or $(C_3-C_9)$-heteroaryl is optionally substituted by 1, 2 or 3 identical or different radicals from the series comprising carboxyl, cyano, amino, nitro, $(C_1-C_4)$-alkylamino, hydroxyl, $(C_1C_4)$-alkoxy, halogen, di-$(C_1-C_4)$ alkylamino, carbamoyl, sulfamoyl and $(C_1-C_4)$-alkoxycarbonyl, and $R^8$ is defined as $R^3$ under c1), and to their physiologically tolerated salts.

$(C_6-C_{12})$-Aryl is to be understood to be, for example, phenyl, naphthyl or biphenylyl. A corresponding statement applies to radicals derived therefrom, such as aroyl.

Alkyl and radicals derived therefrom, such as alkoxy, may be straight-chain or branched.

Halogen preferably represents fluorine, chlorine or bromine.

A heteroaryl radical within the meaning of the present invention is the radical of a monocyclic or bicyclic $(C_3-C_9)$-heteroaromatic compound which contains in the ring system one or two nitrogen atoms and/or one sulfur or one oxygen atom. Concerning the term "heteroaromatic compound" see Garatt, Vollhardt, Aromatizität (Aromaticity) Stuttgart 1973, pages 131–153. Examples of suitable heteroaryl radicals are the radicals of thiophene, furan, benzo[b]-thiophene, benzofuran, pyrrole, imidazole, pyrazole, pyridine, pyrazine, pyrimidine, pyridazine, indole, quinoline, isoquinoline, oxazole, isoxazole, thiazole, isothiazole, isobenzofuran, indolizine, isoindole, indazole, phthalazine, naphthyridine, quinoxaline, quinazoline, cinnoline and furazan. Aryl, alkyl, heteroaryl and radicals derived therefrom may be substituted as indicated once or, if chemically possible, several times.

Unless otherwise indicated, centers of chirality may be present in the R or in the S configuration. The invention relates both to the optically pure compounds and to stereoisomer mixtures such as enantiomer mixtures and diastereomer mixtures.

Particularly suitable salts are alkali metal and alkaline earth metal salts, salts with physiologically tolerated amines, and salts with inorganic or organic acids such as, for example, HCl, HBr, $H_2SO_4$, maleic acid and fumaric acid.

Preferred compounds of the formula I are those in which A denotes optionally substituted $(C_1-C_8)$-alkyl, $(C_1-C_8)$-alkanoyl or optionally substituted $(C_1-C_8)$-alkoxycarbonyl, or is defined as above under a3), those in which $R^8$ denotes hydrogen, and those in which $A^1$ denotes carbonyl, thiocarbonyl or $CR^5R^6$ with $R^5$ and $R^6=H$.

Furthermore, preferred compounds of the formula I are those in which $A^2$ denotes imino, oxy or methylene—particularly preferably imino-, E denotes carbonyl, $A^3$ denotes oxy or a direct bond and/or $R^4$ denotes optionally substituted $(C_6-C_{12})$-aryl or denotes $(C_6-C_{12})$-aryl-$(C_1-C_5)$-alkyl which is optionally substituted in the alkyl moiety and/or optionally substituted in the aryl moiety, suitable substituents in the aryl moiety being, in particular, halogens, pseudohalogens and carboxyl groups, and suitable substituents in the alkyl moiety being, in particular, carboxyl, $(C_1-C_4)$-alkoxycarbonyl and amino groups.

Particularly preferred compounds of the formula I are those in which A represents substituted $(C_1-C_8)$-alkanoyl, examples of suitable substituents being $(C_6-C_{12})$-aryl-$(C_1-C_4)$-alkylsulfonyl and $(C_6-C_{12})$-aryl-$(C_1-C_4)$alkylsulfinyl, or represents a radical of the formula IIa as defined above under a3).

The invention also relates to a process for the preparation of compounds of the formula I, which comprises synthesis of the compounds in a known manner from the fragments, for example by the coupling thereof, where appropriate elimination of one or more temporarily introduced protective group(s), where appropriate conversion of carbonyl groups into the thia analogs, and where appropriate conversion of the resulting compounds of the formula I into their physiologically tolerated salts.

Fragments in the above sense are to be understood to be amino acids, segments containing several amino acids, derivatives of amino acids, derivatives of peptides having modified peptide bonds, as well as carboxylic acids substituted in various ways, various alcohols and their derivatives.

The coupling can be carried out by, for example, condensing, in an inert solvent, a fragment of a compound of the formula I having a terminal carboxyl group, or a reactive acid derivative, with another, appropriate fragment which contains, for example, a free amino group, it being possible for any functional groups which are present and not involved in the reaction to be protected where appropriate, with the formation of an amide bond. Methods suitable for the formation of an amide bond are described in Houben-Weyl, Methoden der organischen Chemie (Methods of Organic Chemistry), volume 15/2.

The process is advantageously carried out in a manner such that a) a compound of the formula IIIa is condensed with a compound of the formula IIIb

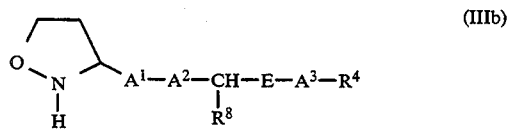
(IIIb)

in which A, B, D, E, F, $R^4$ and $R^8$ are as defined above, and X represents a nucleophilically detachable leaving group such as OH, Cl, Br, I, tosyl, triflate or, if A is an acyl radical, also represents an active ester group, b) a compound of the formula IVa is condensed with a compound of the formula IVb

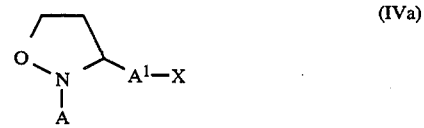
(IVa)

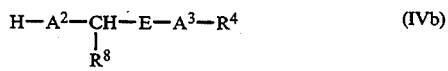
(IVb)

in which A, $A^1$, E, $A^3$, $R^4$ and $R^8$ are as defined above, $A^2$ represents imino, N-methylimino or oxy, and X represents a nucleophilically detachable leaving group such as OH, Cl, Br, I, tosyl, triflate or, if B denotes carbonyl, also represents an active ester group, or c) a compound of the formula Va is condensed with a compound of the formula Vb

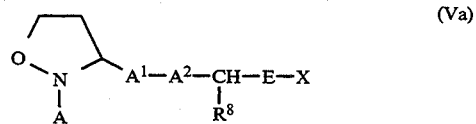
(Va)

(Vb)

in which A, B, D, $R^4$ and $R^8$ are as defined above, E is as defined above, with the exception of hydroxymethylene, $A_3$ denotes oxy, imino or N-methylimino, and X represents a nucleophilically detachable leaving group such as OH, Cl, Br, I, tosyl, triflate or an active ester group.

The reaction of a carboxylic acid of the formula IIIa, IVa or Va with the appropriate compound of the formula IIIb, IVb or Vb having a free amino group is preferably carried out in a solvent customary in peptide chemistry, or in water/solvent mixtures, in the presence of a suitable condensing agent such as, for example, 1. dicyclohexylcarbodiimide with the addition of 1-hydroxybenzotriazole (DCC/HOBt method, lit.: Chem. Ber. 103 (1970) 788)

2. dicyclohexylcarbodiimide with the addition of 3-hydroxy-4-oxo-3,4-dihydro-1,2,3-benzotriazine (DCC/HOObt method; lit.: Chem. Ber. 103 (1970) 2034)
3. dicyclohexylcarbodiimide with the addition of N-hydroxysuccinimide (DCC/HONSu method; lit.: Z. Naturforsch. 21b (1966) 426)
4. alkanephosphonic anhydride such as n-propylphosphonic anhydride (PPA method; lit.: Angew. Chemie Int. Ed. 19 (1980) 133)
5. dialkylphosphinic anhydride such as methylethylphosphinic anhydride (MEPA method; lit.: U.S. Pat. No. 4,426,325).

Suitable solvents used in the process according to the invention are, for reasons of solubility, usually polar solvents such as, for example, dimethylacetamide, dimethylformamide, dimethyl sulfoxide, phosphoric acid tris(dimethylamide), N-methylpyrrolidone, water or mixtures of the said solvents with water. The latter particularly applies to the MEPA process. However, chloroform, methylene chloride or ethyl acetate are also used. The synthesis can be carried out between $-10°$ and about $50°$ C., preferably $-10°$ C. and room temperature. It is preferable to start at about $0°$ C. and subsequently to increase to room temperature.

The condensation of a carboxylic acid of the formula IVa or Va with an alcohol of the formula IVb or Vb, respectively, to give a carboxylic ester can advantageously be carried out by the dicyclohexylcarbodiimide (DCC) method—as described in Angew. Chem. 90, 556 (1978)—in an inert solvent such as DMF, with 4-dimethylaminopyridine catalysis, in the temperature range between $-20°$ and $+40°$ C., preferably $-20°$ C. and room temperature. Methods suitable for the preparation of a modified peptide bond are described in Janssen Chimica Acta, vol. 3, No. 2 [985]. The following methods are preferably used:

Synthesis of derivatives having reduced peptide bonds by reductive amination of aldehydes with amino acid esters using sodium cyanoborohydride (cf. Borch et al., J. Amer. Chem. Soc. 93 [1971]2897; 91 [1969]3996) or by N-alkylation of amines or amino acid derivatives (cf. Houben-Weyl, Methoden der Org. Chemie, vol. 11/1) by d) reacting a compound of the formula VIa, VIb or VIc with a compound of the formula IIIb

A′—CHO (VIa)

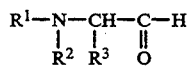
(VIb)

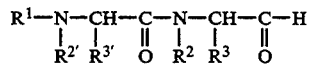
(VIc)

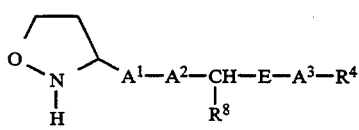
(IIIb)

in which $A^1$, $A^2$, E, $A^3$, $R^1$, $R^2$, $R^{2'}$, $R^3$, $R^{3'}$, $R^4$ and $R^8$ are defined as above, and A′ represents $(C_1-C_8)$-alkyl which is optionally substituted as A under $a_1$), or represents $(C_3-C_8)$-cycloalkyl, $(C_6-C_{12})$-aryl or $(C_3-C_9)$-heteroaryl, which are optionally substituted as A under $a_2$), $e_1$) reacting a compound of the formula VIIa with a compound of the formula IVb

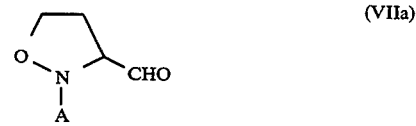
(VIIa)

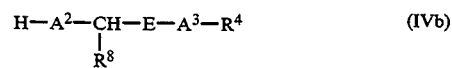
(IVb)

in which A, E, $A^3$, $R^4$ and $R^8$ are as defined above, A additionally represents [2,3:5,6]-diisopropylidenemannofuranosyl, and $A^2$ represents imino or N-methylimino, $e_2$) reacting a compound of the formula VIIIa with a compound of the formula VIIIb

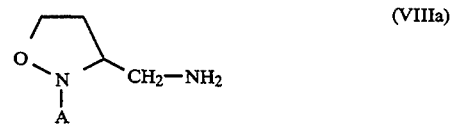
(VIIIa)

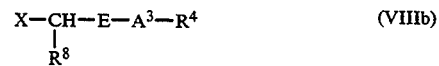
(VIIIb)

in which A, E, $A^3$, $R^4$ and $R^8$ are as defined above, it being possible for A additionally to denote H, and X representing a nucleophilically detachable leaving group such as OH, Cl, Br, I, tosyl or triflate, or $e_3$) in analogy to the process described under b) (page 7) reacting a compound of the formula IVa with a compound of the formula IVb

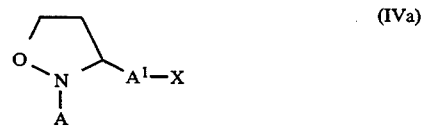
(IVa)

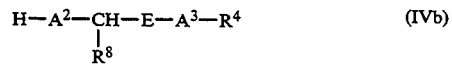
(IVb)

in which A, E, $A^3$, $R^4$ and $R^8$ are as defined above, B represents $-CH_2-$, $A^2$ represents imino, N-methylimino or oxy, and X represents a nucleophilically detachable leaving group such as OH, Cl, Br, I, tosyl or triflate.

The reductive amination is expediently carried out in a lower alcohol having up to 4 carbon atoms, such as methanol, at a temperature between $0°$ C. and the boiling point of the reaction mixture, preferably between $10°$ and $40°$ C., and at a pH of 4–5.

The synthesis of ketomethylene analogs of the formula I, in which $A^1$ denotes CO and $A^2$ denotes $-CH_2-$, is carried out by a Grignard or Reformatsky reaction by f) reacting the components IXa and IXb

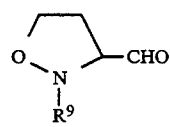
(IVa)

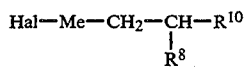
(IXb)

in which $R^8$ preferably denotes H, $R^9$ preferably denotes trityl or [2,3:5,6]-diisopropylidenemannofuranosyl, Me denotes Mg or Zn, and $R^{10}$ denotes a protected carboxyl group which is stable under the conditions of the Grignard reaction, such as oxazolinyl or 2,6,7-trioxabicyclo[2.2.2]octanyl, preferably in an ether such as diethyl ether, dibutyl ether or tetrahydrofuran, at a temperature between $-80°$ C. and the boiling point of the reaction mixture. The resulting alcohol can be oxidized to the ketone by various oxidation processes known from the literature, and the protective group $R^9$ can be removed under acid catalysis. The condensation reactions by the processes a) and c) described on page 7 finally provide the ketomethylene compounds of the formula I.

Endothiopeptides are advantageously obtained by reaction of the compounds of the general type I with Lawesson's reagent (2,4-bis(4-methoxyphenyl)-1,3-dithia-2,4-diphosphetane-2,4-disulfide) (cf. Synthesis 1979, 941).

Protective groups suitable for the temporary protection of other functional groups are those customarily used in peptide synthesis and described, for example, in Kontakte Merck 3/79, pages 14–22 and 1/80, pages 23–35.

Examples of urethane protective groups of the amino group are Pyoc, Fmoc, Fcboc, Z, Boc, Ddz, Bpoc, Z—(NO₂), Dobz, Moc, Mboc, Iboc, Adoc, Adpoc, Msc or Pioc; Z or Boc is preferred. These amino protective groups are removed with acids, bases or by reduction.

Examples of protective groups of the guanidino group are NO₂, tosyl, Boc, Z, mesitylene-2-sulfonyl (Mts) and the like. Elimination can be effected by hydrolysis or hydrogenolysis.

The COOH side groups are blocked as alkyl esters, preferably methyl, ethyl or tert.-butyl esters or as benzyl esters or modified benzyl esters (p-NO₂, p-Cl, p-Br inter alia). Deblocking is effected by alkaline or acid hydrolysis or hydrogenation.

Examples of hydroxyl protective groups are tert.-butyl or benzyl.

The substances according to the invention are active as irreversible inhibitors of prolyl hydroxylase. As a consequence, they bring about selective inhibition of the collagen-specific hydroxylation reaction in the course of which protein-bound proline is hydroxylated by the enzyme prolyl hydroxylase. Prevention of this reaction by an inhibitor results in an underhydroxylated collagen molecule which is incapable of functioning and can be released in only small amounts from the cell into the extracellular space. The underhydroxylated collagen is unable, furthermore, to be incorporated in the collagen matrix and very readily undergoes proteolytic degradation. The consequence of these effects is an overall reduction in the amount of collagen undergoing extracellular deposition. Hence inhibitors of prolyl hydroxylase are suitable tools in the therapy of diseases in which the deposition of collagens makes a decisive contribution to the clinical picture. These include, inter alia, fibroses of lungs, liver and skin (scleroderma) and atherosclerosis.

It is also known that inhibitors of collagen production have antitumor properties. Reduction in the synthesis and deposition of collagen has an effect on the stroma transformation which is necessary for tumor growth (H. Dvorak, N. Engl. J. of Med. 315 (1986) 1650); and the inhibitors of the formation of basement membrane are suitable for suppressing the growth of various tumors (W. Klohs et al. J. N. C. I. 75 (1985) 353).

It is also known that inhibition of prolyl hydroxylase by known inhibitors such as α,α-dipyridyl results in inhibition of C1q biosynthesis by macrophages (W. Müller et al., FEBS Lett. 90, 218f (1978)). The classical pathway of complement activation thus becomes inoperative. Hence inhibitors of prolyl hydroxylase also act as immunosuppressants, for example in immune complex diseases.

Hence the substances according to the invention can be used as fibrosuppressants, immunosuppressants and antiatheroscleroticis and in tumor therapy.

The inhibitory action can be determined in an enzyme assay analogous to the method of B. Peterkofsky and R. DiBlasio Anal. Biochem. 66, 279–286 (1975). This entails underhydroxylated collagen being enzymatically hydroxylated with prolyl hydroxylase in the presence of iron(II) ions, α-ketoglutarate and ascorbate.

The suicidal nature of the inhibition is established by preincubation of the enzyme in the presence of iron(II) ions, α-ketoglutarate and ascorbate with the inhibitors for various times, and then determination of the remaining activity of the enzyme in the presence of a peptide substrate. It is possible to use for determination of the activity both the method of Peterkofsky and DiBlasio described above and other methods such as described by K. I. Kivirikko and R. Myllylä, Meth. Enzym. 82, 245–304 (1982). Table 1 lists the inhibitory action of some selected compounds according to the invention. The concentration which inactivates 50% of the enzyme after one hour is stated.

TABLE 1

| Compound | ID₅₀ [60 min; μmol/l] |
|---|---|
| Ac—Pro—Opr—Gly—OtBu | 8000.0 |
| Ac—Pro—Opr—Gly—OBzl | 60.0 |
| Z—Ala—Opr—Gly—OtBu | 40.0 |
| Z—Ala—Opr—Gly—OH | 330.0 |
| Ac—Pro—Opr—Gly—NH—CH₂—CH₂—C₆H₅ | 4900.0 |
| Ac—Pro—Opr—Gly—N(C₂H₅)₂ | 16900.0 |
| Ac—Pro—Opr—Gly—NH—CH₂—C₆H₅ | 6000.0 |
| Z—Ala—Opr—Gly—OBzl | 3.0 |
| Z—(D)—Ala—Opr—Gly—OBzl | >10000.0 |
| Z—Phe—Opr—Gly—OBzl | 0.8 |
| Msc—Glu(OBzl)—Opr—Gly—OBzl | 30.0 |
| Z—Val—Opr—Gly—OBzl | 40.0 |

TABLE 1-continued

| Compound | $ID_{50}$ [60 min; $\mu$mol/l] |
|---|---|
| Z—Glu—Opr—Gly—OBzl | 5000.0 |
| $C_6H_5$—$CH_2$—CO—Opr—Gly—OBzl | 1000.0 |
| $C_6H_5$—$CH_2$—CO—Opr—Gly—O—$CH_2$—$C_6H_4$-4-$NO_2$ | 540.0 |
| Z—Phe—Opr—NH—$CH_2$—CO—$CH_2$—$CH_2$—$C_6H_5$ | 3.4 |
| $C_6H_5$—$CH_2$—$CH_2$—CO—Opr—Gly—OBzl | 2000.0 |
| Z—Tyr—Opr—Gly—OBzl | 2.4 |
| Z—Phe—Opr—Sar—OBzl | >10000.0 |
| Z—Lys(Pht)—Opr—Gly—OBzl | 11.0 |
| Z—Phe—Opr—NH—$CH_2$—CO—$C_6H_5$ | 2.4 |
| $C_6H_5$—$CH_2$—Opr—Gly—OBzl | 610.0 |
| Z—Phe(r)—Opr—Gly—OBzl | 1.1 |
| H—Phe—Opr—NH—$CH_2$—CO—$C_6H_4$-4-Cl | 15.5 |
| Z—Phe—Opr—NH—$CH_2$—CO—$C_6H_4$-4-CN | 1.1 |
| Z—Phe—Opr—Gly—O—$CH_2$—$C_6H_4$-4-F | 0.8 |
| Z—Phe—Opr—Gly—O—$CH_2$—$CH_2$—$C_6H_5$ | 0.9 |
| Z—Tic—Opr—Gly—OBzl | 1.5 |

The inhibitory action can also be determined in cell or tissue culture. It is possible to use for this purpose fibroblasts or other collagen-producing cells, or calvariae or other collagen-producing organs. Table 2 is a compilation of the inhibitory action of some substances according to the invention in calvarial culture. The concentration which results in a 50% decrease in the hydroxyproline/proline quotient on feeding with $^{14}C$-proline is stated.

TABLE 2

| Compound | $IC_{50}$ [$\mu$M] |
|---|---|
| Z—Ala—Opr—Gly—OBzl | 1650 |
| Ac—Pro—Opr—Gly—OtBu | 7500 |
| Z—Val—Opr—Gly—OBzl | 380 |
| Z—Pro—Opr—Gly—OtBu | 550 |
| $C_6H_5$—$CH_2$—CO—Opr—Gly—OBzl | 2000 |
| Z—Ala—Opr—Gly—OBzl | 2500 |
| $C_6H_5$—$CH_2$—CO—Opr—Gly—$OCH_2$—$C_6H_4$-4-$NO_2$ | 2500 |

The antifibrotic action can be determined in the model of liver fibrosis induced by carbon tetrachloride. This entails rats being treated twice a week with $CCl_4$ (1 ml/kg) dissolved in olive oil. The test substance is administered orally or intraperitoneally—dissolved in a suitable tolerated solvent—once a day or, where appropriate, twice a day. Histological determination of the extent of liver fibrosis is carried out; the proportion of collagen in the liver is analyzed by hydroxyproline determination—as described by Kivirikko et al. (Anal. Biochem. 19, 249 f, (1967)). The fibrogenesis activity can be determined by radioimmunological determination of collagen fragments and procollagen peptides in the serum. The compounds according to the invention are active in concentrations of 1–100 mg/kg in this model. Another model for evaluating the anti-fibrotic action is that of bleomycin-induced pulmonary fibrosis as described by Kelley et al. (J. Lab. Clin. Med. 96, 954, (1980)). The action of the compounds according to the invention on granulation tissue can be evaluated by using the cotton pellet granuloma model as described by Meier et al., Experientia 6, 469 (1950).

Hence the invention relates to the use of a compound of the formula I as inhibitor of prolyl hydroxylase, and to the use thereof as medicine in mammals and in humans, in particular as fibrosuppressants, immunosuppressants and antiatherosclerotics and in tumor therapy.

The invention also relates to pharmaceutical compositions which contain an effective amount of a compound of the formula I and a physiologically acceptable vehicle, and to a process for the preparation of these compositions, which comprises converting the active substance together with the vehicle and, where appropriate, other auxiliaries or additives into a suitable form for administration. The proportion of active substance in these compositions is 0.1 to 96% as a rule.

Administration can be intranasal, buccal, intravenous, subcutaneous or oral. The dosage of the active substance depends on the warm-blooded species, the body weight and age, and the mode of administration.

The pharmaceutical products of the present invention are produced in dissolution, mixing, granulating or tablet-coating processes known per se.

For a form for oral administration, the active compounds are mixed with the additives customary for this purpose, such as excipients, stabilizers or inert diluents and converted by customary methods into suitable forms for administration, such as tablets, coated tablets, hard gelatin capsules, aqueous, alcoholic or oily suspensions, or aqueous, alcoholic or oily solutions. Examples of suitable inert vehicles are gum arabic, magnesium carbonate, potassium phosphate, lactose, glucose or starch, especially corn starch. The preparation in this connection can be carried out both as dry and as wet granules. Examples of suitable oily excipients or solvents are vegetable or animal oils, such as sunflower oil or fish liver oil.

For subcutaneous or intravenous administration, the active compounds or their physiologically tolerated salts are converted into a solution, suspension or emulsion, if desired with the substances customary for this purpose, such as solubilizers or other auxiliaries. Examples of those suitable for this purpose are: water, physiological saline solution or alcohols, for example ethanol, propanol and glycerol, as well as sugar solutions such as glucose or mannitol solutions, or a mixture of the various solvents mentioned.

The examples which follow serve to illustrate the present invention without intending to confine it to them.

List of abbreviations used:

| AA | amino acid analysis |
|---|---|
| Ac | acetyl |
| Boc | tert.-butoxycarbonyl |
| TLC | thin-layer chromatography |
| DCC | dicyclohexylcarbodiimide |
| DCU | dicyclohexylurea |
| DMF | dimethylformamide |
| DMSO | dimethyl sulfoxide |
| EA | ethyl acetate |
| FAB | fast atom bombardment |
| Fmoc | 9-fluorenylmethyloxycarbonyl |

| | -continued |
|---|---|
| HOBt | 1-hydroxybenzotriazole |
| HPhe | homophenylalanine |
| M | molecular peak |
| MeOH | methanol |
| MS | mass spectrum |
| CHN | elemental analysis |
| NEM | N-ethylmorpholine |
| tBu | tert.-butyl |
| Pht | phthalyl |
| m.p. | melting point |
| THF | tetrahydrofuran |
| Z | benzyloxycarbonyl |
| h | hour |
| min | minute |
| RT | room temperature |
| Tic | 1,2,3,4-tetrahydroisoquinoline |
| Phg | phenylglycine |

The other abbreviations used for amino acids and protective groups correspond to the letter code customary in peptide chemistry, as is described in, for example, Europ. J. Biochem. 138, 9–37 (1984). Unless expressly indicated otherwise, the amino acids are always in the L configuration.

The abbreviation Opr is introduced, consistent with the customary three-letter code, for the unnatural amino acid 5-oxaproline (=isoxazolidine-3-carboxylic acid).

Thus Opr, H-Opr-OH, Opr(r) and Opr(t) correspond to the following structures

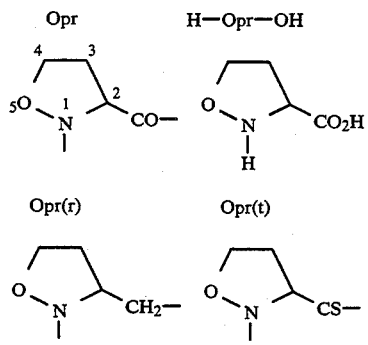

H-Opr-OtBu is synthesized in analogy to the literature procedure in J. C. S. Chem. Commun. 1981, 97–99.

Chromatography solvent systems:

| 1. CHCl$_3$/MeOH | 9:1 |
|---|---|
| 2. EA/petroleum ether | 2:1 |
| 3. EA/petroleum ether | 1:1 |
| 4. EA/petroleum ether | 4:1 |
| 5. EA/petroleum ether | 3:1 |
| 6. CHCl$_3$/CH$_3$OH | 11:1 |
| 7. CHCl$_3$//CH$_3$OH/EA | 10:2:1 |

EXAMPLES

A.1. Z-Phe-Opr-Gly-OBzl

A.1.1. Z-Phe-Opr-OtBu 600 mg of the hydrochloride of H-Opr-OtBu, 860 mg of Z-Phe-OH, 0.36 ml of NEM and 395 mg of HOBt are dissolved in DMF. 590 mg of DCC are added, and the mixture is then left to react at room temperature for 28 h. The solvent is evaporated, the residue is dissolved in 20 ml of EA, and the solution is extracted by shaking, in each case 3 times, with 20 ml of 20% strength aqueous citric acid and then with 20 ml of saturated aqueous sodium bicarbonate solution. The organic phase is dried over sodium sulfate, filtered, and the solvent is evaporated off. 1.20 g of Z-Phe-Opr-OtBu are isolated as a colorless powder. Without purification the crude product is immediately subjected to the next reaction step (A.1.2.).

A.1.2. Z-Phe-Opr-OH 1.20 g of Z-Phe-Opr-OtBu are dissolved in 10 ml of trifluoroacetic acid. The solution is stirred at RT for 1 h, the solvent is evaporated off under high vacuum, and the residue is chromatographed on silica gel (system 7). 800 mg of Z-Phe-Opr-OH are isolated; R$_f$ (system 7)=0.2; MS (FAB): 399 (M+1).

A.1.3. Z-Phe-Opr-Gly-OBzl 800 mg of Z-Phe-Opr-OH, 640 mg of the hydrochloride of H-Gly-OBzl, 260 μl of NEM, 270 mg of HOBt and 415 mg of DCC are dissolved in 20 ml of DMF, and the solution is stirred at RT for 18 h. The solvent is evaporated off in vacuo. The residue is chromatographed on silica gel (system 3). 520 mg of Z-Phe-Opr-Gly-OBzl are isolated as an amorphous solid. R$_f$(system 3)=0.39; MS (FAB): 546 (M+1)

The compounds of the Examples A.2. to A.62 are synthesized by peptide coupling in analogy to the procedure described in Example A.1.1., there being first N-terminal linkage of an amino acid to H-Opr-OtBu, then hydrolysis of the ester, and addition of the second amino acid.

| Example No. | |
|---|---|
| A.2. | Z—Ala—Opr—Gly—OBzl |
| A.3. | Z—(D)—Ala—Opr—Gly—OBzl |
| A.4. | Z—Ala—Opr—Gly—OtBU |
| A.5. | Z—Ala—Opr—Gly—OH |
| A.6. | Z—Arg—Opr—Gly—OBzl |
| A.7. | Z—Arg(Z$_2$)—Opr—Gly—OBzl |
| A.8. | Z—Asp—Opr—Gly—OBzl |
| A.9. | Z—Asn—Opr—Gly—OBzl |
| A.10. | Msc—Asn—Opr—Gly—OBzl |
| A.11. | Z—Dab—Opr—Gly—OBzl |
| A.12. | Z—Cys(Acm)—Opr—Gly—OBzl |
| A.13. | Z—Cys(Bzl)—Opr—Gly—OBzl |
| A.14. | Z—Cys—Opr—Gly—OBzl |
| A.15. | Z—Gln—Opr—Gly—OBzl |
| A.16. | Z—Gln—Opr—Gly—O—CH$_2$—C$_6$H$_4$ (p-NO$_2$) |
| A.17. | Z—Glu(OBzl)—Opr—Gly—OBzl |
| A.18. | Z—Glu—Opr—Gly—OBzl |
| A.19. | Z—Gly—Opr—Gly—OBzl |
| A.20. | Z—His—Opr—Gly—OBzl |
| A.21. | Z—Ile—Opr—Gly—OBzl |
| A.22. | Z—Leu—Opr—Gly—OBzl |
| A.23. | Msc—Leu—Opr—Gly—OBzl |
| A.24. | Z—Lys(Msc)—Opr—Gly—OBzl |
| A.25. | Z—Lys(Pht)—Opr—Gly—OBzl |
| A.26. | Z—Lys—Opr—Gly—OBzl |
| A.27. | Z—Orn—Opr—Gly—OBzl |
| A.28. | H—Phe—Opr—Gly—OBzl |
| A.29. | Z—Phe—Opr—Gly—O—CH$_2$—C$_6$H$_4$-4-F |
| A.30. | Z—Phe—Opr—(D)—Ala—OBzl |
| A.31. | Z—Phe—Opr—Sar—OBzl |
| A.32. | Ac—Pro—Opr—Gly—OBzl |
| A.33. | Z—Pro—Opr—Gly—OBzl |
| A.34. | Ac—Pro—Opr—Gly—OtBu |
| A.35. | Z—Pro—Opr—Gly—OtBu |
| A.36. | Z—Opr—Opr—Gly—OBzl |
| A.37. | Z—Opr—Opr—Gly—O—CH$_2$—C$_6$H$_4$-4-Cl |
| A.38. | Z—Ser—Opr—Gly—OBzl |
| A.39. | Z—Thr(Bzl)—Opr—Gly—OBzl |
| A.40. | Z—Thr—Opr—Gly—OBzl |
| A.41. | Z—Tyr(CH$_3$)—Opr—Gly—OBzl |
| A.42. | Z—Tyr—Opr—Gly—OBzl |
| A.43. | Z—Trp—Opr—Gly—OBzl |
| A.44. | Z—Val—Opr—Gly—OBzl |
| A.45. | Z—Phe—Opr—Gly—O—CH$_2$—CH$_2$—C$_6$H$_5$ |

-continued

| Example No. | |
|---|---|
| A.46. | Z—Tic—Opr—Gly—OBzl |
| A.47. | Z—Phe—Opr—Gly—OEt |
| A.48. | Z—Phe—Opr—Gly—(O—CH$_2$—CH$_2$)$_3$—OCH$_3$ |
| A.49. | Z—Phe—Opr—Gly—O—CH(C$_6$H$_5$)$_2$ |
| A.50. | Z—Phe—Opr—Gly—O—CH$_2$—(C$_5$H$_4$N) |
| A.51. | Z—Phe—Opr—Gly—O—CH$_2$—C$_6$H$_4$-2-F |
| A.52. | Z—Phe—Opr—Gly—O—CH$_2$—C$_6$H$_4$-3-F |
| A.53. | Z—Phe—Opr—Gly—O—CH$_2$—C$_6$H$_4$-4-F |
| A.54. | Z—Phe—Opr—Gly—O—(CH$_2$)$_3$—C$_6$H$_5$ |
| A.55. | Z—Phe—Opr—Gly—O—(CH$_2$)$_2$—C$_6$H$_4$-4-F |
| A.56. | Z—(4'-Cl)Phe—Opr—Gly—OBzl |
| A.57. | Z—(4'-F)Phe—Opr—Gly—OBzl |
| A.58. | Z—(4'-NO$_2$)Phe—Opr—Gly—OBzl |
| A.59. | Z—Phe—Opr—Gly—O—CH$_2$—CH(CO$_2$Et)—CH$_2$—C$_6$H$_5$ |
| A.60. | Z—Phe—Opr—Gly—O—CH$_2$—CH(COOH)—CH$_2$—C$_6$H$_5$ |
| A.61. | Z—Phg—Opr—Gly—OBzl |
| A.62. | Z—HPhe—Opr—Gly—OBzl |

Various types of analytical and spectroscopic methods were used to confirm the structures of the peptides prepared in this way. Some results are compiled in Table 3.

TABLE 3

(Analytical data on the tripeptides A—Opr—A$^1$ (Examples A.1. to A.62.))
$^1$H-NMR: δ [ppm] =

| No. | 2-H(Opr) | 3-H$_2$(Opr) | 4-H$_2$(Opr) | 2-H(A) | 3-H$_x$(A) | 2-H$_y$(A$^1$) | Others |
|---|---|---|---|---|---|---|---|
| A.1. | 4.85 | 2.5–2.7 | 3.95–4.2 | 5.1 | 3.1 | 3.95 | MS; CHN |
| A.2. | 4.75 | 2.55–4.2 | 3.95–4.2 | 4.85 | 1.45 | 4.05 | MS; CHN |
| A.3. | 4.8 | 2.55–2.8 | 3.9–4.05 | 4.2 | 1.35 | 3.95 | MS; CHN |
| A.4. | 4.75 | 2.55–2.9 | 3.9–4.1 | 4.8 | 1.45 | 4.0 | MS; CHN |
| A.5. | 4.75 | 2.5–2.75 | 3.9–4.1 | 4.8 | 1.45 | 4.05 | MS |
| A.6. | 4.8 | 2.5–2.75 | 3.95–4.1 | 4.85 | 1.75 | 4.0 | MS |
| A.7. | 4.8 | 2.5–2.75 | 3.9–4.1 | 4.75 | 1.75 | 4.0 | MS; CHN |
| A.8. | 4.8 | 2.55–2.7 | 3.9–4.15 | 4.9 | 2.8 | 3.9 | MS |
| A.9. | 4.75 | 2.55–2.7 | 3.9–4.1 | 4.85 | 2.7 | 3.95 | MS |
| A.10. | 4.9 | 2.55–2.7 | 3.9–4.1 | 4.9 | 2.65 | 4.0 | MS; CHN |
| A.11. | 4.9 | 2.5–2.75 | 3.95–4.1 | 4.9 | 2.1 | 3.95 | MS |
| A.12. | 4.8 | 2.55–1.8 | 3.9–4.15 | 4.95 | 3.1 | 4.0 | MS |
| A.13. | 4.85 | 2.55–2.75 | 3.9–4.1 | 4.95 | 3.0 | 3.95 | MS |
| A.14. | 4.85 | 2.55–2.75 | 3.9–4.05 | 5.0 | 3.05 | 3.95 | MS; CHN |
| A.15. | 4.85 | 2.55–2.75 | 3.95–4.1 | 4.9 | 2.45 | 3.95 | MS; CHN |
| A.16. | 4.85 | 2.55–2.75 | 3.95–4.1 | 4.9 | 2.5 | 4.0 | MS |
| A.17. | 4.7 | 2.5–2.7 | 3.9–4.1 | 4.85 | 2.2 | 4.0 | MS; CHN |
| A.18. | 4.85 | 2.55–2.7 | 3.9–4.15 | 4.8 | 2.2 | 4.05 | MS; CHN |
| A.19. | 4.95 | 2.5–2.7 | 3.9–4.1 | 4.1 | — | 4.0 | MS; CHN |
| A.20. | 4.9 | 2.5–2.75 | 3.9–4.15 | 4.9 | 3.2 | 3.95 | MS |
| A.21. | 4.9 | 2.55–2.7 | 3.95–4.1 | 4.85 | 2.0 | 4.0 | MS |
| A.22. | 4.9 | 2.5–2.85 | 4.0–4.05 | 4.9 | 1.95 | 4.05 | MS |
| A.23. | 4.8 | 2.50–2.8 | 3.95–4.1 | 4.95 | 1.9 | 4.0 | MS |
| A.24. | 4.85 | 2.55–2.8 | 3.95–4.2 | 4.8 | 1.8 | 4.1 | MS; CHN |
| A.25. | 4.75 | 2.5–2.75 | 3.9–4.05 | 4.9 | 1.85 | 4.05 | MS |
| A.26. | 4.9 | 2.55–2.75 | 3.85–4.15 | 4.9 | 1.85 | 4.05 | MS; CHN |
| A.27. | 4.9 | 2.5–2.75 | 3.9–4.05 | 4.85 | 2.05 | 4.0 | MS |
| A.28. | 4.85 | 2.55–2.80 | 3.9–4.1 | 4.25 | 2.95 | 3.95 | MS |
| A.29. | 4.85 | 2.5–2.75 | 3.9–4.15 | 5.0 | 3.1 | 3.95 | MS; CHN |
| A.30. | 5.05 | 2.5–2.7 | 3.9–4.2 | 4.8 | 3.1 | 4.55 | MS; CHN |
| A.31. | 4.95 | 2.5–2.65 | 4.0–4.3 | 5.1 | 3.1 | 3.75; 4.6 | MS; CHN |
| A.32. | 4.95 | 2.55–2.65 | 4.05–4.15 | 5.0 | 2.1 | 4.05 | MS; CHN |
| A.33. | 4.9 | 2.5–2.6 | 3.6–4.0 | 4.9 | 2.1 | 3.95 | MS; CHN |
| A.34. | 4.9 | 2.55–2.7 | 3.8–3.85 | 4.85 | 2.1 | 4.1 | MS; CHN |
| A.35. | 4.9 | 2.5–2.65 | 3.65–4.0 | 5.05 | 2.1 | 4.0 | MS; CHN |
| A.36. | 4.9 | 2.5–2.7 | 3.75–3.95 | 5.0 | 2.6 | 4.1 | MS |
| A.37. | 4.8 | 2.55–2.7 | 3.7–4.0 | 5.0 | 2.55 | 4.0 | MS |
| A.38. | 4.9 | 2.5–2.7 | 3.75–4.05 | 5.0 | 2.75 | 4.0 | MS |
| A.39. | 4.95 | 2.5–2.75 | 3.9–4.15 | 5.05 | 3.9 | 4.0 | MS |
| A.40. | 4.95 | 2.5–2.7 | 3.9–4.1 | 4.85 | 3.9 | 4.0 | MS; CHN |
| A.41. | 4.8 | 2.5–2.7 | 3.9–4.15 | 4.9 | 3.1 | 3.95 | MS |
| A.42. | 4.85 | 2.5–2.7 | 3.9–4.15 | 4.9 | 3.0 | 4.05 | MS; CHN |
| A.43. | 4.95 | 2.5–2.65 | 3.9–4.1 | 4.95 | 3.0 | 4.05 | MS; CHN |
| A.44. | 4.7 | 2.55–2.7 | 3.9–4.1 | 4.9 | 2.1 | 4.05 | MS; CHN |
| A.45. | 4.85 | 2.5–2.7 | 3.9–4.15 | 5.0 | 3.0 | 4.05 | MS; CHN |
| A.46. | 4.8 | 2.5–2.75 | 3.85–4.1 | 5.1 | 3.0–3.25 | 3.95 | MS; CHN |
| A.47. | 4.8 | 2.5–2.8 | 3.9–4.2 | 4.8 | 3.0–3.3 | 3.9 | MS; CHN |
| A.48. | 4.85 | 2.5–2.85 | 3.9–4.25 | 5.1 | 3.0–3.2 | 4.0 | MS; CHN |
| A.49. | 4.85 | 2.5–2.8 | 3.85–4.2 | 5.05 | 3.1 | 3.9–4.15 | MS; CHN |
| A.50. | 4.85 | 2.5–2.8 | 3.9–4.15 | 5.1 | 3.1 | 4.05 | MS; CHN |
| A.51. | 4.85 | 2.5–2.8 | 3.9–4.15 | 5.05 | 3.1 | 3.95 | MS; CHN |
| A.52. | 4.8 | 2.5–2.75 | 3.9–4.2 | 5.05 | 3.1 | 3.95 | MS; CHN |
| A.53. | 4.8 | 2.5–2.8 | 3.9–4.2 | 5.1 | 3.1 | 3.95 | MS; CHN |
| A.54. | 4.85 | 2.45–2.8 | 3.9–4.2 | 5.1 | 3.0–3.2 | 3.9 | MS; CHN |
| A.55. | 4.8 | 2.5–2.8 | 3.9–4.2 | 5.1 | 3.0–3.2 | 3.95 | MS; CHN |
| A.56. | 4.8 | 2.5–2.9 | 3.9–4.25 | 5.1 | 3.0–3.3 | 4.0–4.2 | MS; CHN |
| A.57. | 4.8 | 2.5–2.85 | 3.9–4.25 | 5.1 | 3.05–3.3 | 4.0–4.2 | MS; CHN |
| A.58. | 4.8 | 2.5–2.9 | 3.9–4.3 | 5.1 | 3.1–3.35 | 4.0–4.2 | MS; CHN |
| A.59. | 4.9 | 2.45–2.8 | 3.95–4.2 | 5.1 | 3.1–3.3 | 4.0 | MS; CHN |
| A.60. | 4.8 | 2.5–2.8 | 3.85–4.2 | 5.1 | 3.0–3.3 | 4.0 | MS; CHN |
| A.61. | 4.9 | 2.5–2.8 | 3.9–4.2 | 5.8 | — | 3.95 | MS; CHN |

TABLE 3-continued (Analytical data on the tripeptides A—Opr—A$^1$ (Examples A.1. to A.62.))
$^1$H-NMR: δ [ppm] =

| No. | 2-H(Opr) | 3-H$_2$(Opr) | 4-H$_2$(Opr) | 2-H(A) | 3-H$_x$(A) | 2-H$_y$(A$^1$) | Others |
| --- | --- | --- | --- | --- | --- | --- | --- |
| A.62. | 4.75 | 2.4–2.8 | 3.8–4.2 | 4.85 | 1.8–2.1 | 3.9–4.1 | MS; CHN |

B.1. 4-Nitrobenzyl ester of N-phenylacetyl-Opr-Gly

B.1.1. N-Phenylacetyl-Opr-OtBu 490 mg of DCC are added to 500 mg of the hydrochloride of H-Opr-OtBu, 324 mg of phenylacetic acid, 320 mg of HOBt and 300 μl of NEM in 10 ml of DMF, and the mixture is stirred at RT for 48 h. The urea is filtered off, the solvent is evaporated off in vacuo, the residue is dissolved in ethyl acetate, and the solution is washed with aqueous citric acid and aqueous sodium bicarbonate solution. Drying over sodium sulfate and removal of the solvent in vacuo is followed by isolation of 600 mg of the slightly impure target compound N-phenylacetyl-Opr-OtBu.

B.1.2. N-Phenylacetyl-Opr-OH 600 mg of the crude product from B.1.1. are dissolved in 5 ml of trifluoroacetic acid, and the solution is stirred at RT for 1 h. Concentration under high vacuum is followed by recrystallization from EA. 250 mg of N-phenylacetyl-Opr-OH are isolated. R$_f$(system 7)=0.65; MS (FAB) : 235 (M+1).

B.1.3. 4-Nitrobenzyl ester of N-phenylacetyl-Opr-Gly 70 mg of N-phenylacetyl-Opr-OH, 87 mg of the hydrobromide of H-Gly-OBzl-NO$_2$, 40 μl of NEM and 41 mg of HOBt are dissolved in DMF. 62 mg of DCC are then added, and the mixture is stirred at RT for 8 h. The solvent is evaporated off and then chromatography is carried out on silica gel (system 5). R$_f$(system 5)=0.43; MS (FAB): 428 (M+1).

The compounds of Examples B.2. to B.19 are synthesized in analogy to the procedure described in Example B.1., there being first N-terminal coupling of the carboxylic acid onto H-Opr-OtBu, then hydrolysis of the ester and linkage of the C-terminal unit.

| Example No.: | |
| --- | --- |
| B.2. | N-Benzoyl-Opr—Gly—OBzl |
| B.3. | N-4-Chlorobenzoyl-Opr—Gly—OBzl |
| B.4. | N-2-Fluorobenzoyl-Opr—Gly—OBzl |
| B.5. | N-3-Hydroxyphenylacetyl-Opr—Gly—OBzl |
| B.6. | N-4-Fluorophenylacetyl-Opr—Gly—OBzl |
| B.7. | N-Benzyloxycarbonyl-Opr—Gly—OBzl |
| B.8. | N-3-Phenylpropionyl-Opr—Gly—OBzl |
| B.9. | N-Phenoxyacetyl-Opr—Gly—OBzl |
| B.10. | N-4-Phenylbutyryl-Opr—Gly—OBzl |
| B.11. | N-4,4-Di-p-Fluorophenylbutyryl-Opr—Gly—OBzl |
| B.12. | N-Diphenylacetyl-Opr—Gly—OBzl |
| B.13. | Pivaloyl-Opr—Gly—OBzl |
| B.14. | N-(3-Phenylpropionyl)-Opr—Gly—OCH$_2$—C$_6$H$_4$-4-NO$_2$ |
| B.15. | 4-CH$_3$—C$_6$H$_4$—SO$_2$—Opr—Gly—OBzl |
| B.16. | N-Phenylacetyl-Opr—Gly—O—CH(CH$_3$)$_2$ |
| B.17. | N-(2-Acetoxy-3-phenylpropionyl)—Opr—Gly—OBzl |
| B.18. | N-(2-Hydroxy-3-phenylpropionyl)—Opr—Gly—OBzl |
| B.19. | N-[C$_6$H$_5$—(CH$_2$)$_2$—CO—O—CH(CH$_2$—C$_6$H$_5$)—CO]—Opr—Gly—OBzl |

TABLE 4

(Analytical data on the dipeptides A-Opr-Gly-OR)
(Examples B.2.–B.19.)
$^1$H-NMR: δ [ppm] =

| No. | 2-H(Opr) | 3-H$_2$(Opr) | 4-H$_2$(Opr) | CH$_2$(Gly) | CH$_x$—CO(A) | Others |
| --- | --- | --- | --- | --- | --- | --- |
| B.1. | 4.85 | 2.45–2.85 | 3.65–4.15 | 4.1 | 3.8 | MS; CHN |
| B.2. | 4.9 | 2.5–2.8 | 3.65–4.1 | 4.0 | — | MS; CHN |
| B.3. | 4.95 | 2.55–2.8 | 3.65–4.05 | 4.05 | — | MS; CHN |
| B.4. | 4.9 | 2.5–2.8 | 3.65–4.1 | 4.0 | — | MS; CHN |
| B.5. | 4.85 | 2.5–2.8 | 3.65–4.1 | 4.05 | 3.75 | MS; CHN |
| B.6. | 4.9 | 2.5–2.8 | 3.65–4.15 | 4.05 | 4.0 | MS; CHN |
| B.7. | 4.9 | 2.5–2.8 | 3.65–4.1 | 4.0 | 5.2 | MS; CHN |
| B.8. | 4.85 | 2.45–2.7 | 3.55–4.1 | 4.05 | 2.7 | MS; CHN |
| B.9. | 4.9 | 2.5–2.8 | 3.6–4.1 | 4.05 | 4.7 | MS; CHN |
| B.10. | 4.9 | 2.5–2.75 | 3.6–4.1 | 4.0 | 2.7 | MS; CHN |
| B.11. | 4.9 | 2.5–2.8 | 3.6–4.1 | 4.05 | 2.65 | MS; CHN |
| B.12. | 4.85 | 2.55–1.85 | 3.65–4.05 | 4.05 | 5.05 | MS; CHN |
| B.13. | 4.9 | 2.5–2.8 | 3.6–4.05 | 4.0 | — | MS; CHN |
| B.14. | 4.85 | 2.45–2.75 | 3.6–4.1 | 4.1 | 3.7 | MS; CHN |
| B.15. | 4.15 | 2.5–2.75 | 3.7–4.05 | 4.2 | — | MS; CHN |
| B.16. | 4.85 | 2.45–2.8 | 3.7–4.1 | 4.1 | 3.8 | MS; CHN |
| B.17. | 4.9 | 2.5–2.8 | 4.0–4.25 | 4.1 | 5.6 | MS; CHN |
| B.18. | 4.95 | 2.5–2.8 | 4.0–4.2 | 4.0 | 4.0 | MS; CHN |
| B.19. | 4.9 | 2.5–2.8 | 3.8–4.1 | 4.0 | 5.5 | MS; CHN |

C.1. N-4-Fluorobenzyl-Opr-Gly-OBzl

C.1.1. N-4-Fluorobenzyl-Opr-OH 30 mg of sodium cyanoborohydride are added to 145 mg of 4-fluorobenzaldehyde and 150 mg of the hydrochloride of H-Opr-OtBu in 20 ml of dry methanol. The pH of the solution is maintained at 4.0 by addition of 0.01N methanolic HCl. The mixture is stirred at RT for 6 h, then concentrated almost to dryness in vacuo, the residue is taken up in 100 ml of 2N aqueous HCl, and the solution is heated at 50° C. for 30 min, allowed to cool and extracted with EA. The organic solution is dried over magnesium sulfate and then filtered, the solvent is evaporated in vacuo, and the residue is chromatographed on silica gel (system 7). 160 mg of N-4-fluorobenzyl-Opr-OH are isolated as a white solid. $R_f$(system 7)=0.15; MS (FAB): 226 (M+1).

C.1.2. N-4-Fluorobenzyl-Opr-Gly-OBzl 160 mg of N-4-fluorobenzyl-Opr-OH, 105 mg of H-Gly-OBzl, 100 µl of NEM, 100 mg of HOBt and 150 mg of DCC are dissolved in 10 ml of anhydrous DMF, and the solution is stirred at RT for 24 h. It is concentrated in vacuo, the residue is taken up in 20 ml of methylene chloride, the DCU is filtered off, and the filtrate is again concentrated. Chromatography on silica gel (system 3) is followed by isolation of 180 mg of N-4-fluorobenzyl-Opr-Gly-OBzl. $R_f$ (system 3)=0.45; MS (FAB): 373 (M+1).

The compounds of Examples C.2. to C.6. are synthesized in analogy to the procedure described in Example C.1.

| Example No. | |
|---|---|
| C.2. | $C_6H_5$—$CH_2$-Opr-Gly-OBzl |
| C.3. | 4-Cl—$C_6H_4$—$CH_2$-Opr-Gly-OBzl |
| C.4. | 4-$CH_3$—$C_6H_4$—$CH_2$-Opr-Gly-OBzl |
| C.5. | 4-$CH_3O$—$C_6H_4$—$CH_2$-Opr-Gly-OBzl |
| C.6. | Z-Phe(r)-Opr-Gly-OBzl |

TABLE 5

(Analytical data on the dipeptides of Examples C.1.-C.6.)
$^1$H-NMR: δ [ppm] =

| No. | 2-H(Opr) | 3-$H_2$(Opr) | 4-$H_2$(Opr) | $CH_2$(Gly) | Others |
|---|---|---|---|---|---|
| C.1. | 4.1 | 2.55–2.8 | 3.85–4.05 | 4.05 | MS; CHN |
| C.2. | 4.1 | 2.5–2.8 | 3.9–4.1 | 4.05 | MS; CHN |
| C.3. | 4.05 | 2.5–2.8 | 3.85–4.05 | 4.0 | MS |
| C.4. | 4.05 | 2.5–2.8 | 3.9–4.05 | 4.05 | MS |
| C.5. | 4.05 | 2.55–2.8 | 3.9–4.1 | 4.05 | MS |
| C.6. | 4.05 | 2.5–2.75 | 3.85–4.05 | 4.05 | MS; CHN |

D. 1. Z-Phe-Opr-NH—$CH_2$—CO—$CH_2$—$CH_2$—$C_6H_5$

D.1.1. (D,L)-4-Phenyl-2-hydroxy-1-butylamine 6.70 g of dihydrocinnamaldehyde are dissolved in 20 ml of anhydrous ethanol, and 10 ml of nitromethane and 1 ml of tetramethylguanidine are added, and the mixture is stirred at RT for 1 h. It is concentrated in vacuo, the residue is taken up in 200 ml of ethanol and 5 ml of glacial acetic acid, 10 g of activated Raney nickel are added and the mixture is then hydrogenated at 50° C. and under 25 bar $H_2$ pressure for 5 h. The catalyst is then filtered off, the filtrate is concentrated in vacuo, the residue is taken up in saturated aqueous sodium bicarbonate solution, and non-polar impurities are removed by extraction with diethyl ether. Extraction 3 times with tetrahydrofuran, drying over sodium sulfate, and concentration in vacuo provides 5.75 g of (D,L)-4-phenyl-2-hydroxy-1-butylamine as a colorless oil.

D.1.2. Z-Phe-Opr-NH—$CH_2$—CHOH—$CH_2$—$CH_2$—$C_6H_5$ 843 mg of Z-Phe-Opr-OH, 700 mg of 4-phenyl-2-hydroxy-1butylamine, 285 mg of HOBt and 436 mg of DCC are dissolved in 10 ml of DMF. 270 µl of NEM are added, and the mixture is then left to react at RT for 18 h. The solvent is evaporated in vacuo, the residue is dissolved in ethyl acetate, and the solution is treated 3 times with aqueous citric acid solution and with saturated aqueous sodium bicarbonate solution. The solution is dried over sodium sulfate and then filtered and evaporated. Chromatography on silica gel (system 4) is carried out to isolate 680 mg of the target compound. $R_f$(system 4)=0.35; MS (FAB): 6 (M+1).

D.1.3. Z-Phe-Opr-NH—$CH_2$—CO—$CH_2$—$CH_2$—$C_6H_5$ 200 mg of Z -Phe-Opr-NH—$CH_2$—CHOH—$CH_2$—$CH_2$—$C_6H_5$ are dissolved in 20 ml of anhydrous methylene chloride, 800 mg of pyridinium chlorochromate are added, and then the mixture is stirred at RT for 6 h. It is concentrated in vacuo, and the chromium salts and small amounts of additional compounds which have been produced are removed by chromatography on silica gel (system 4). 128 mg of the ketone are isolated. $R_f$(system 4)=0.68; MS (FAB): 544 (M+1).

Compounds D.2. to D.28. are prepared in analogy to the procedure described in Example D.1.

| Example No. | |
|---|---|
| D.2. | Z—Phe—Opr—NH—$CH_2$—CO—$C_6H_5$ |
| D.3. | Z—Phe—Opr—NH—$CH_2$—CO—$C_6H_4$-4-OH |
| D.4. | Z—Phe—Opr—NH—$CH_2$—CO—$C_6H_4$-4-$OCH_3$ |
| D.5. | Z—Phe—Opr—NH—$CH_2$—CO—$CH_2$—$C_6H_5$ |
| D.6. | Z—Phe—Opr—NH—$CH_2$—CO—$CH_2$—$C_6H_4$-4-OH |
| D.7. | Z—Phe—Opr—NH—$CH_2$—CO—$CH_2$—$CH_2$—$C_6H_4$-4-Cl |
| D.8. | Z—Phe—Opr—NH—$CH_2$—CO—$CH_2$—$CH_2$—$CH_2$—$C_6H_5$ |
| D.9. | Z—Phe—Opr—NH—$CH_2$—CO—$C_6H_4$-4-$CH(CH_3)_2$ |
| D.10. | $C_6H_5$—CO—Opr—NH—$CH_2$—CO—$CH_2$—$C_6H_5$ |
| D.11. | Z—Phe—Opr—NH—$CH_2$—CO—$C_6H_4$-4-CN |
| D.12. | H—Phe—Opr—NH—$CH_2$—CO—$C_6H_4$-4-Cl |
| D.13. | Z—Phe—Opr—NH—$CH_2$—CO— 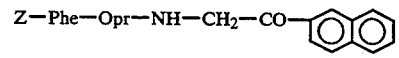 |
| D.14. | Z—Phe—Opr—NH—$CH_2$—CO—$C_6H_4$-4-Cl |

-continued

| Example No. | |
|---|---|
| D.15. | Z—Phe—Opr—NH—CH$_2$—CO—C$_6$H$_4$-4-F |
| D.16. | Z—Phe—Opr—NH—CH$_2$—CO—C$_6$H$_4$-4-CF$_3$ |
| D.17. | Z—Phe—Opr—NH—CH$_2$—CO—C$_6$H$_4$-4-COOH |
| D.18. | Z—Phe—Opr—NH—CH$_2$—CO—C$_6$H$_4$-3-CN |

D.19.

N—[C$_6$H$_5$—(CH$_2$)$_2$—CO—O—CH(CH$_2$—C$_6$H$_5$)—CO]—Opr—Gly—⟨⟩—Cl

| D.20. | N-(2-Acetoxy-3-phenylpropionyl)-Opr—NH—CH$_2$—CO—C$_6$H$_4$—Cl |
|---|---|
| D.21. | N-(2-Hydroxy-3-phenylpropionyl)-Opr—NH—CH$_2$—CO—C$_6$H$_4$—Cl |
| D.22. | Z—Phe—Opr—NH—CH$_2$—CO—C$_6$H$_4$-4-CO$_2$CH$_3$ |
| D.23. | Boc—Phe—Opr—NH—CH$_2$—CO—C$_6$H$_4$-4-Cl |
| D.24. | Z—Glu—Opr—NH—CH$_2$—CO—C$_6$H$_4$-4-Cl |
| D.25. | Z—Cys—Opr—NH—CH$_2$—CO—C$_6$H$_4$-4-Cl |
| D.26. | Z—Phe—Opr—NH—CH$_2$—CO—CH$_2$—CH(CO$_2$Et)—CH$_2$—C$_6$H$_5$ |
| D.27. | C$_6$H$_5$—(CH$_2$)$_2$—SO$_2$—CH$_2$—CH(CH$_2$—C$_6$H$_5$)—CO—Opr—NH—CH$_2$—CO—C$_6$H$_4$-4-CN |
| D.28. | C$_6$H$_5$—(CH$_2$)$_2$—SO$_2$—CH$_2$—CH(CH$_2$—C$_6$H$_5$)—CO—Opr—NH—CH$_2$—CO—CH$_2$—CH(CH$_2$—C$_6$H$_5$)—CO$_2$C$_2$H$_5$ |

TABLE 6

(Analytical data on the dipeptides of Examples D.1.–D.28.
$^1$H-NMR: δ [ppm] =

| No. | 2-H(Opr) | 3-H$_2$(Opr) | 4-H$_2$(Opr) | N—CH$_2$—CO | Others |
|---|---|---|---|---|---|
| D.1. | 4.9 | 2.55–2.7 | 3.95–4.2 | 4.0 | MS; CHN |
| D.2. | 5.1 | 2.6–2.8 | 3.95–4.25 | 4.7 | MS; CHN |
| D.3. | 5.0 | 2.55–2.7 | 3.9–4.2 | 4.6 | MS; CHN |
| D.4. | 4.9 | 2.5–2.7 | 3.9–4.15 | 4.6 | MS |
| D.5. | 5.0 | 2.55–2.7 | 3.9–4.1 | 4.1 | MS; CHN |
| D.6. | 5.0 | 2.55–2.7 | 3.95–4.05 | 4.05 | MS |
| D.7. | 5.0 | 2.55–2.7 | 3.9–4.15 | 4.1 | MS; CHN |
| D.8. | 4.9 | 2.55–2.7 | 3.9–4.15 | 4.0 | MS; CHN |
| D.9. | 5.1 | 2.6–2.8 | 3.95–4.2 | 4.7 | MS; CHN |
| D.10. | 4.9 | 2.5–2.8 | 3.65–4.1 | 4.15 | MS; CHN |
| D.11. | 4.9 | 2.6–2.8 | 3.95–4.25 | 4.7 | MS; CHN |
| D.12. | 4.95 | 2.5–2.7 | 3.9–4.15 | 4.65 | MS; CHN |
| D.13. | 4.9 | 2.5–2.85 | 3.9–4.3 | 4.85 | MS; CHN |
| D.14. | 4.9 | 2.5–2.7 | 3.95–4.3 | 4.6–4.8 | MS; CHN |
| D.15. | 4.95 | 2.55–2.85 | 3.9–4.3 | 4.7 | MS; CHN |
| D.16. | 4.9 | 2.45–2.8 | 3.9–4.3 | 4.7 | MS; CHN |
| D.17. | 4.9 | 2.50–2.85 | 3.9–4.25 | 4.7 | MS; CHN |
| D.18. | 4.9 | 2.5–2.85 | 3.9–4.25 | 4.7 | MS; CHN |
| D.19. | 4.9 | 2.5–2.75 | 3.9–4.2 | 4.6–4.8 | MS; CHN |
| D.20. | 4.9 | 2.45–2.8 | 3.9–4.25 | 4.7 | MS; CHN |
| D.21. | 4.95 | 2.5–2.8 | 3.9–4.3 | 4.6–4.8 | MS; CHN |
| D.22. | 4.9 | 2.5–2.85 | 3.9–4.3 | 4.7 | MS; CHN |
| D.23. | 4.9 | 2.5–2.85 | 3.9–4.3 | 4.65 | MS; CHN |
| D.24. | 4.75 | 2.5–2.8 | 3.8–4.25 | 4.55 | MS; CHN |
| D.25. | 4.95 | 2.55–2.85 | 3.9–4.3 | 4.6–4.8 | MS; CHN |
| D.26. | 5.0 | 2.5–2.75 | 3.9–4.3 | 4.1 | MS; CHN |
| D.27. | 4.9 | 2.5–2.8 | 3.9–4.25 | 4.7 | MS; CHN |
| D.28. | 4.9 | 2.5–2.75 | 3.9–4.35 | 4.1 | MS; CHN |

E.1. Z-Phe-Opr(t)-Gly-OBzl 800 mg of Z-Phe-Opr-Gly-OBzl are mixed with 350 mg of Lawesson's reagent, and the mixture is suspended in 10 ml of anhydrous benzene. A homogeneous solution is obtained on heating to 80° C. The solution is stirred at this temperature for 1 h, concentrated in vacuo, and the residue is chromatographed on silica gel (system 3). 210 mg of the thioamide Z-Phe-Opr(t)-Gly-OBzl (R$_f$(system 3)=0.45; MS (FAB): 562 (M+1))and 62 mg of the thioamide Z-Phe(t)-Opr-Gly-OBzl (R$_f$ (system 3)=0.61; MS (FAB): 562 (M+1)) are isolated.

The compounds E.2. and E.3. are prepared in analogy to the procedure described in Example E.1.

| Example No. | |
|---|---|
| E.2. | Z-Phe-Opr(t)-NH—CH$_2$—CO—CH$_2$—C$_6$H$_5$ |

-continued

| Example No. | |
|---|---|
| E.3. | 4-F—C$_6$H$_4$—CO-Opr(t)-NH—CH$_2$—CO—CH$_2$—C$_6$H$_4$-4-Cl |

TABLE 7

(Analytical data on the dipeptides of Examples E.1.–E.3.)
$^1$H-NMR: δ [ppm] =

| No. | 2-H (Opr)(t) | 3-H$_2$ (Opr(t)) | 4-H$_2$ (Opr(t)) | N—CH$_2$—CO | Others |
|---|---|---|---|---|---|
| E.1. | 5.2 | 2.55–2.75 | 3.95–4.2 | 4.1 | MS |
| E.2. | 5.1 | 2.5–2.7 | 3.9–4.25 | 4.15 | MS |
| E.3. | 5.0 | 2.55–2.1 | 3.75–4.1 | 4.05 | MS |

F. The synthesis of the compounds of the general structural type A-Opr(r)-Gly-F-R⁴ is carried out by one of the processes described under e₁), e₂) or e₃) (page 10) depending on the radicals A, F and R⁴.

| Example No. | |
|---|---|
| F.1. | Z-Phe-Opr(r)-Gly-O-Bzl |
| F.2. | Z-Phe-Opr(r)-Gly-O-CH₂—C₆H₄-4-Cl |
| F.3. | Z-Phe-Opr(r)-NH-CH₂—CO—C₆H₅ |
| F.4. | Z-Phe-Opr(r)-NH—CH₂—CO—C₆H₄-4-OH |
| F.5. | Z-Phe-Opr(r)-NH—CH₂—CO—C₆H₄-4-OCH₃ |
| F.6. | Z-Phe-Opr(r)-NH—CH₂—CO—CH₂—C₆H₆ |
| F.7. | Z-Phe-Opr(r)-NH—CH₂—CO—CH₂—C₆H₄-4-Cl |
| F.8. | Z-NH—CH(C₆H₅)—CO-Opr(r)-NH—CH₂—CO—CH₂—C₆H₆ |
| F.9. | C₆H₅—CH₂—CH₂—CO—O—CH(CH₂—C₆H₅)—CO-Opr(r)-NH—CH₂—CO—C₆H₄-4-CN |
| F.10. | C₆H₅—CH₂—CH₂—SO₂—CH₂—CH(CH₂—C₆H₅)—CO-Opr(r)-NH—CH₂—CO—C₆H₄-4-Cl |
| F.11. | C₆H₅—CH₂—CH₂—SO—CH₂—CH(CH₂—C₆H₅)—CO-Opr(r)-NH—CH₂—CO—C₆H₄-4-Cl |
| F.12. | C₆H₅—CH₂—CH₂—SO₂—CH₂—CH(CH₂—C₆H₅)—CO-Opr(r)-NH—CH₂—CO—CH₂—CH(CH₂—C₆H₅)—CO₂C₂H₅ |
| F.13. | C₆H₅—CH₂—CH₂—SO₂—CH₂—CH(CH₂—C₆H₅)—CO-Opr(r)-NH—CH₂—CO—CH₂—CH(CH₂—C₆H₅)—COOH |

G. The synthesis of ketomethylene analogs of the general

A=Opr-CH₂—CH₂—CO—F—R⁴ is carried out by the

| Example No. | |
|---|---|
| G.1. | Z-Phe-Opr-CH₂—CH₂—CO—CH₂—C₆H₅ |
| G.2. | Z-Phe-Opr-CH₂—CH₂—CO—C₆H₅ |
| G.3. | Z-Phe-Opr-CH₂—CH₂—CO—C₆H₄—4-OCH₃ |
| G.4. | Z-Phe-Opr-CH₂—CH₂—CO—CH₂—C₆H₄-4-OCH₃ |
| G.5. | Z-Phe-Opr-CH₂—CH₂—CO—CH₂—C₆H₄ |
| G.7. | Z-NH—CH(C₆H₅)—CO-Opr-CH₂—CH₂—CO—CH₂—C₆H₅ |
| G.8. | Z-Trp-Opr-CH₂—CH₂—CO—CH₂—C₆H₅ |

TABLE 9

(Analytical data on the dipeptides of Examples G.1.-G.8.)

¹H-NMR: δ [ppm] =

| No. | 2-H(Opr) | 3-H₂(Opr) | 4-H₂(Opr) | Others |
|---|---|---|---|---|
| G.1. | 5.2 | 2.55–2.75 | 3.9–4.15 | MS; CHN |
| G.2. | 5.1 | 2.55–2.8 | 3.85–4.05 | MS |
| G.3. | 5.2 | 2.55–2.75 | 3.85–4.1 | MS |
| G.4. | 5.2 | 2.55–2.75 | 3.8–4.05 | MS; CHN |
| G.5. | 5.1 | 2.55–2.8 | 3.8–4.05 | MS |
| G.6. | 5.15 | 2.55–2.8 | 3.8–4.1 | MS |
| G.7. | 5.2 | 2.55–2.75 | 3.9–4.1 | MS |
| G.8. | 5.2 | 2.5–2.8 | 3.8–4.0 | MS |

We claim:

1. A compound of the formula I

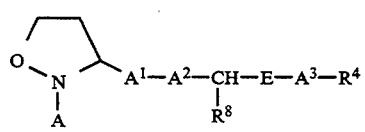

in which

A is a radical of the formula IIa

in which

R¹ is $(C_1-C_8)$-alkanoyl or $(C_1-C_8)$-alkoxycarbonyl which are unsubstituted or are substituted in the alkyl chain by 1 or 2 radicals selected from the group consisting of hydroxyl and $(C_6-C_{12})$-aryl, or which are monosubstituted in the alkyl chain by a radical selected from the group consisting of $(C_4-C_4)$-alkylsulfonyl, $(C_6-C_{12})$-aryl-$(C_1-C_4)$-alkylsulfonyl, $(C_6-C_{12})$-aryl-$(C_1-C_4)$-alkylsulfinyl, $(C_6-C_{12})$-aryloxy and $(C_6-C_{12})$-aryl-$(C_1-C_5)$-alkyl, wherein each $(C_6-C_{12})$-aryl is unsubstituted or substituted by 1 or 2 radicals selected from the group consisting of halogen, hydroxyl and $(C_1-C_4)$-alkoxy;

R² is hydrogen;

R³ is hydrogen, phenyl or $(C_1-C_6)$-alkyl which is unsubstituted or monosubstituted by a radical selected from the group consisting of amino, hydroxyl, carboxyl, carbamoyl, guanidino, ureido, mercapto, methylmercapto, phenyl, 4-chlorophenyl, 4-fluorophenyl, 4-nitrophenyl, 4-methoxyphenyl, 4-hydroxyphenyl, phthalimido and cyclohexyl;

A¹ is carbonyl;

A² is imino or N-methylimino;

E is carbonyl;

A³ is oxy or a direct bond;

R⁴ is $(C_1-C_6)$-alkyl, $(C_6-C_{12})$-aryl or $(C_6-C_{12})$-aryl-$(C_1-C_5)$-alkyl, in which each alkyl can be substituted by 1 or 2 radicals selected from the group consisting of carboxyl, $(C_1-C_4)$-alkoxy, $(C_1-C_4)$-alkoxycarbonyl, $(C_6-C_{12})$-aryl and $(C_6-C_{12})$-aryl-$(C_1-C_5)$-alkyl, and in which each $(C_6-C_{12})$-aryl is substituted by a radical selected from the group consisting of carboxyl, cyano, nitro, hydroxyl, $(C_1-C_4)$-alkoxy, halogen and $(C_1-C_4)$alkoxycarbonyl; and R⁸ is hydrogen;

or a physiologically tolerated salt thereof.

2. A compound of the formula I as claimed in claim 1 in which A² is imino.

3. A compound of the formula I as claimed in claim 1, in which R⁴ is unsubstituted or substituted $(C_6-C_{12})$-aryl or is $(C_6-C_{12})$-aryl-$(C_1-C_5)$-alkyl or $(C_6-C_{12})$-aryl-$(C_1-C_5)$-alkyl which is substituted in the alkyl moiety and/or substituted in the aryl moiety.

4. A pharmaceutical composition comprising a compound of the formula I as claimed in claim 1 or a physiologically tolerated salt thereof in an amount effective for the treatment of fibroses of the lungs, liver and skin, together with a physiologically acceptable vehicle.

5. A pharmaceutical composition comprising a compound of the formula I as claimed in claim 1 or a physiologically tolerated salt thereof in an amount effective for the treatment of atherosclerosis, together with a physiologically acceptable vehicle.

6. A method for inhibiting prolyl hydroxylase which comprises administering to a host an amount effective for said inhibiting of a compound of the formula I as claimed in claim 1 or a physiologically tolerated salt thereof.

7. A method for the treatment of fibroses of the lungs, liver and skin, which comprises administering to a host an amount effective for said treatment of a compound of the formula I as claimed in claim 1 or a physiologically tolerated salt thereof.

8. A method for the treatment of atherosclerosis, which comprises administering to a host an amount effective for said treatment of a compound of the formula I as claimed in claim 1 or a physiologically tolerated salt thereof.

9. The compound of the formula I as claimed in claim 1, which is Z-Ala-Opr-Gly-OBzl.

10. The compound of the formula I as claimed in claim 1, which is Z-Phe-Opr-Gly-OBzl.

11. The compound of the formula I as claimed in claim 1, which is Z-Phe-Opr-NH—$CH_2$—CO—$CH_2$—$CH_2$—$C_6H_5$.

12. The compound of the formula I as claimed in claim 1, which is Z-Tyr-Opr-Gly-OBzl.

13. The compound of the formula I as claimed in claim 1, which is Z-Phe-Opr-NH—$CH_2$—CO—$C_6H_5$.

14. The compound of the formula I as claimed in claim 1, which is Z-Phe-Opr-NH—$CH_2$—CO—$C_6H_4$-4-CN.

15. The compound of the formula I as claimed in claim 1, which is Z-Phe-Opr-Gly-O—$CH_2$—$C_6H_4$-4-F.

16. The compound of the formula I as claimed in claim 1, which is Z-Phe-Opr-Gly-O—$CH_2$—$CH_2$—$C_6H_5$.

17. The compound of the formula I as claimed in claim 1, which is Msc-Asn-Opr-Gly-OBzl.

18. The compound of the formula I as claimed in claim 1, which is Msc-Leu-Opr-Gly-OBzl.

19. The compound of the formula I as claimed in claim 1, which is Z-Phg-Opr-Gly-OBzl.

* * * * *

UNITED STATES PATENT AND TRADEMARK OFFICE
CERTIFICATE OF CORRECTION

PATENT NO. : 5,422,342

DATED : June 6, 1995

INVENTOR(S) : Stephan HENKE et al.

It is certified that error appears in the above-indentified patent and that said Letters Patent is hereby corrected as shown below:

Claim 1, col. 22, line 14 should read -- $(C_1-C_4)$-alkylsulfonyl, $(C_6-C_{12})$-aryl-$(C_1-C_4)$-al- --;

col. 22, line 43, "$(C_1-C_4)$alkoxycarbo-" should read --$(C_1-C_4)$-alkoxycarbo- --.

Claim 14, col. 24, line 6, "$C_6H_44-$" should read --$C_6H_4-4-$ --.

Claim 15, col. 24, line 9, "$C_6H_44-F$" should read --$C_6H_4-4-F$-- .

Signed and Sealed this

Nineteenth Day of January, 1999

Attest:

Attesting Officer

*Acting Commissioner of Patents and Trademarks*